United States Patent
Rakow et al.

(10) Patent No.: US 8,537,358 B2
(45) Date of Patent: Sep. 17, 2013

(54) MULTILAYER COLORIMETRIC SENSOR ARRAYS

(75) Inventors: Neal A. Rakow, Woodbury, MN (US); Michael S. Wendland, North St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 107 days.

(21) Appl. No.: 13/320,948

(22) PCT Filed: May 19, 2010

(86) PCT No.: PCT/US2010/035387
§ 371 (c)(1), (2), (4) Date: Nov. 17, 2011

(87) PCT Pub. No.: WO2010/135417
PCT Pub. Date: Nov. 25, 2010

(65) Prior Publication Data
US 2012/0062893 A1 Mar. 15, 2012

Related U.S. Application Data

(60) Provisional application No. 61/180,492, filed on May 22, 2009.

(51) Int. Cl.
*G01N 21/25* (2006.01)
*G01N 21/55* (2006.01)

(52) U.S. Cl.
USPC .................. 356/405; 356/244; 356/445

(58) Field of Classification Search
USPC ........... 356/445, 404–408, 244, 246; 422/56, 422/58, 68.1, 82.05, 119; 428/463, 461, 428/522; 359/585; 436/164
See application file for complete search history.

(56) References Cited

U.S. PATENT DOCUMENTS

| 4,641,524 A | 2/1987 | Tarvin |
| 4,820,649 A | 4/1989 | Kawaguchi |
| 5,611,998 A | 3/1997 | Aussenegg |
| 5,783,836 A | 7/1998 | Liu |

(Continued)

FOREIGN PATENT DOCUMENTS

| RU | 2 181 487 | 4/2002 |
| RU | 2-315-999 | 1/2008 |

(Continued)

OTHER PUBLICATIONS

International Search Report, PCT/US2010/035387, mailed Dec. 23, 2010, 3 pages.

(Continued)

*Primary Examiner* — Sang Nguyen
(74) *Attorney, Agent, or Firm* — Kenneth B. Wood

(57) ABSTRACT

Herein are disclosed methods and devices for detecting the presence of an analyte. Such methods and devices may comprise an array comprising at least two sensing elements that differ in their response to an analyte of interest. The sensing elements each comprise at least an optically responsive layer that comprises at least a highly analyte-responsive sublayer. At least one sensing element of the array further contains a minimally analyte-responsive sublayer that comprises part of the thickness of the optically responsive layer. Methods of making and using such arrays of sensing elements are also disclosed.

27 Claims, 5 Drawing Sheets

(56) References Cited

U.S. PATENT DOCUMENTS

| | | | |
|---|---|---|---|
| 6,007,904 A | 12/1999 | Schwotzer | |
| 6,083,628 A * | 7/2000 | Yializis | 428/463 |
| 6,130,748 A | 10/2000 | Kruger | |
| 6,455,001 B1 * | 9/2002 | Knappe et al. | 422/429 |
| 6,573,305 B1 * | 6/2003 | Thunhorst et al. | 521/50.5 |
| 7,368,294 B2 | 5/2008 | Nikitin | |
| 7,449,146 B2 | 11/2008 | Rakow | |
| 8,163,561 B2 * | 4/2012 | Fontaine et al. | 436/164 |
| 8,350,451 B2 * | 1/2013 | Bright et al. | 313/110 |
| 2004/0062682 A1 | 4/2004 | Rakow | |
| 2004/0184948 A1 | 9/2004 | Rakow | |
| 2007/0140907 A1 | 6/2007 | Rakow | |
| 2007/0297944 A1 | 12/2007 | Wendland | |
| 2008/0063575 A1 | 3/2008 | Rakow | |
| 2008/0063874 A1 | 3/2008 | Rakow | |
| 2011/0254568 A1 | 10/2011 | Thomas | |
| 2011/0257038 A1 | 10/2011 | Thomas | |
| 2011/0257281 A1 | 10/2011 | Thomas | |
| 2012/0003484 A1 * | 1/2012 | Roehrig et al. | 428/447 |

FOREIGN PATENT DOCUMENTS

| | | |
|---|---|---|
| WO | WO 00/29830 | 5/2000 |
| WO | WO 2004/031760 | 4/2004 |
| WO | WO 2007/075273 | 7/2007 |
| WO | WO 2008/033647 | 3/2008 |

OTHER PUBLICATIONS

U.S. Appl. No. 13/320,925, entitled *Multilayer Colorimetric Sensor*, filed May 19, 2010.

* cited by examiner

MULTILAYER COLORIMETRIC SENSOR ARRAYS

CROSS REFERENCE TO RELATED APPLICATIONS

This application is a national stage filing under 35 U.S.C. 371 of PCT/US2010/035387, filed May 19, 2010, which claims priority to U.S. Provisional Application No. 61/180,492, filed May 22, 2009, the disclosure of which is incorporated by reference in its/their entirety herein.

BACKGROUND

The ability to detect chemical analytes, for example organic chemical analytes, is important in many applications, including environmental monitoring and the like. Such detection and/or monitoring of analytes may find particular use in, for example, personal monitors (e.g., that can be worn or carried by a person), and/or area monitors (e.g., that can be placed in a desired environment).

Many methods for the detection of chemical analytes have been developed, for example optical, gravimetric, microelectromechanical, and colorimetric. Though colorimetric devices currently exist for a range of analytes, most are based upon employing dyes or colored chemical indicators for detection. Such compounds are typically selective, meaning that multiple sensors may be necessary in order to detect various classes of compounds. Moreover, many of these systems have lifetime limitation issues, due to photo-bleaching or undesirable side reactions. Many such systems also rely on complicated or bulky optoelectronic components to carry out the optical interrogation.

SUMMARY OF THE INVENTION

Herein are disclosed methods and devices for detecting the presence of an analyte. Such methods and devices may comprise an array comprising at least two sensing elements that differ in their response to an analyte of interest. The sensing elements each comprise at least an optically responsive layer that comprises at least a highly analyte-responsive sublayer. At least one sensing element of the array further contains a minimally analyte-responsive sublayer that comprises part of the thickness of the optically responsive layer.

Thus in one aspect, disclosed herein is an array for optically detecting an analyte, the array comprising at least two individually optically interrogatable sensing elements, wherein each sensing element comprises an optically responsive layer between two reflective layers, wherein the optically responsive layer of each sensing element comprises at least a highly analyte-responsive first sublayer, and wherein the optically responsive layer of at least one of the sensing elements further comprises a minimally analyte-responsive second sublayer, wherein the first sublayer and the second sublayer of each sensing element each comprise a thickness, and wherein the thickness of the first sublayer and of the second sublayer of one sensing element are significantly different from the thickness of the first sublayer and of the second sublayer, respectively, of another sensing element.

Thus in another aspect, disclosed herein is an optical method of detecting an analyte in a monitored atmosphere, comprising: providing an array comprising at least a first sensing element that changes from a first appearance to a second appearance in the presence of a first, lower concentration of analyte in the monitored atmosphere and that changes from the second appearance back to the first appearance in the presence of a second, higher concentration of analyte; and, at least a second sensing element that does not change from a first appearance to a second appearance in the presence of the first, lower concentration of analyte; that in the presence of a third, intermediate concentration of analyte that is between the lower and higher concentrations, changes from a first appearance to a second appearance; and that in the presence of the second, higher concentration of analyte does not change from the second appearance back to the first appearance; and, exposing the array of sensing elements to an atmosphere potentially containing the analyte.

These and other aspects of the invention will be apparent from the detailed description below. In no event, however, should the above summaries be construed as limitations on the claimed subject matter, which subject matter is defined solely by the attached claims, as may be amended during prosecution.

Like reference symbols in the various figures indicate like elements. Unless otherwise indicated, all figures and drawings in this document are not to scale and are chosen for the purpose of illustrating different embodiments of the invention. In particular the dimensions of the various components are depicted in illustrative terms only, and no relationship between the dimensions of the various components should be inferred from the drawings, unless so indicated. Although terms such as "top", "bottom", "upper", "lower", "under", "over", "front", "back", "outward", "inward", "up" and "down", and "first" and "second" may be used in this disclosure, it should be understood that those terms are used in their relative sense only unless otherwise noted. In particular, the characterization of certain parameters (e.g., concentration) in a given context as being "lower", "intermediate" and/or "higher" should be understood to be interpreted in a relative (comparative) sense within the given context (e.g., an "intermediate" concentration is between a "lower" and a "higher" concentration referred to in the same context).

DETAILED DESCRIPTION

Figure 5:
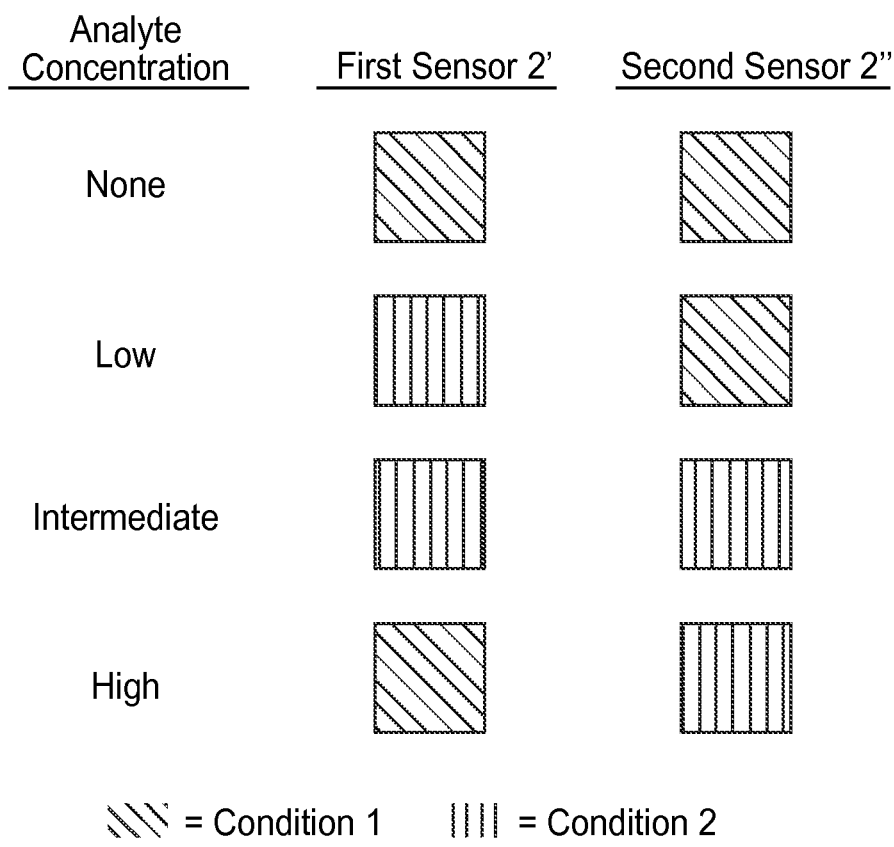
FIG. 5 is a representative depiction of the response of an exemplary array of two sensing elements to various analyte concentrations in a monitored atmosphere.
Figure 6:
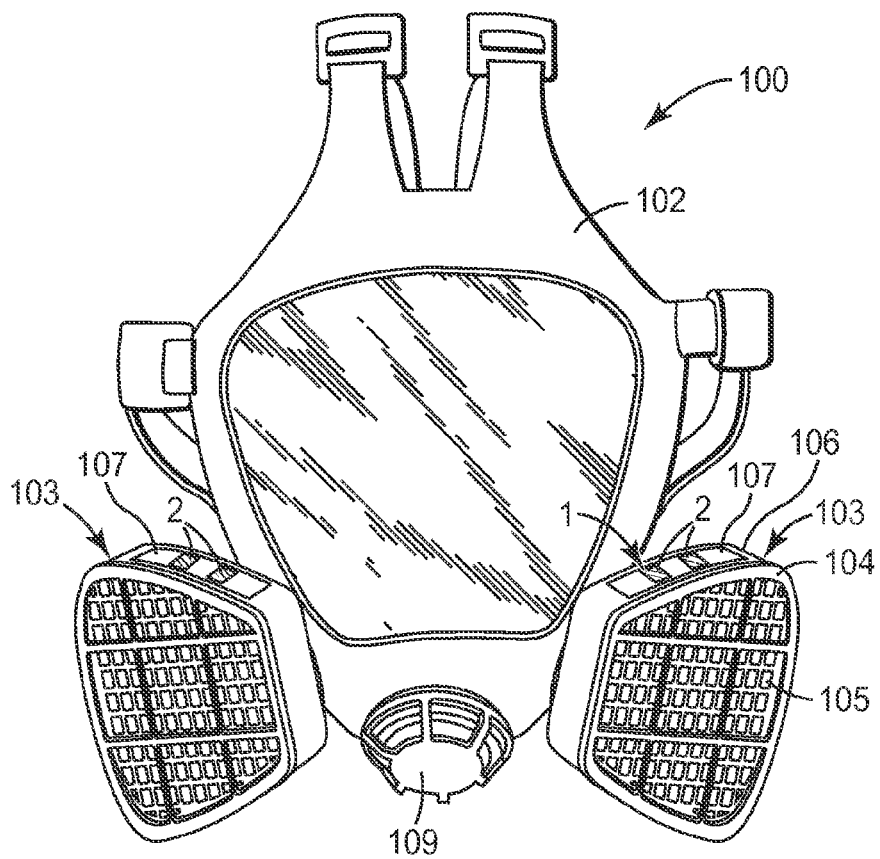
FIG. 6 is a perspective view of a respirator with replaceable sorbent cartridges comprising an array of sensing elements.

Disclosed herein is array 1 which comprises at least first and second sensing elements 2' and 2" (e.g., as shown in an exemplary manner in FIGS. 5 and 6). Each of the sensing elements comprises an optically responsive layer 230, described later herein in detail. Layer 230 in second sensing element 2" differs from layer 230 in first sensing element 2' such that second sensing element 2" responds differently from first sensing element 2' to at least a particular concentration of an analyte of interest (this and all other references to concentration herein refer to the concentration of an analyte in an atmosphere to which the sensing elements are exposed).

Specifically, second sensing element 2" does not optically respond (e.g., by a shift in the reflectance spectrum of at least 15 nm and/or by a visually observable change, both as described later herein in detail) to a particular, lower concentration of analyte that first sensing element 2' optically responds to, and does optically respond to a different, higher concentration of analyte. First sensing element 2' thus being responsive to a lower concentration of analyte, and second sensing element 2" thus being responsive to a higher concentration of analyte, an array comprised of at least the two sensing elements may be able to optically respond over a wider dynamic range (of analyte concentration) than can any single sensing element. In some embodiments, array 1 comprises a plurality of sensing elements (e.g., three, four, five, six, or more), which may provide a further enhanced dynamic range. The use of such arrays as described herein may provide other advantages as well, as will be described in detail.

Figure 1:
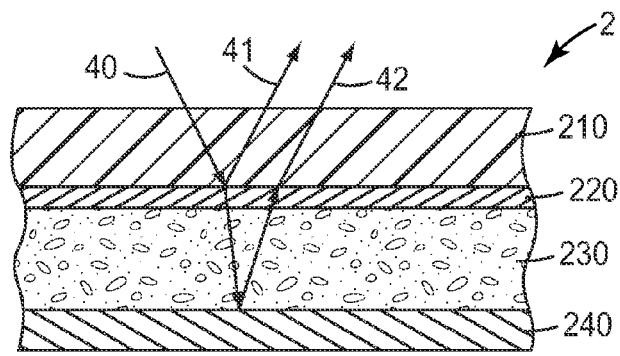
FIG. 1 is a side cross sectional view of a portion of an exemplary sensing element.
Figure 2:
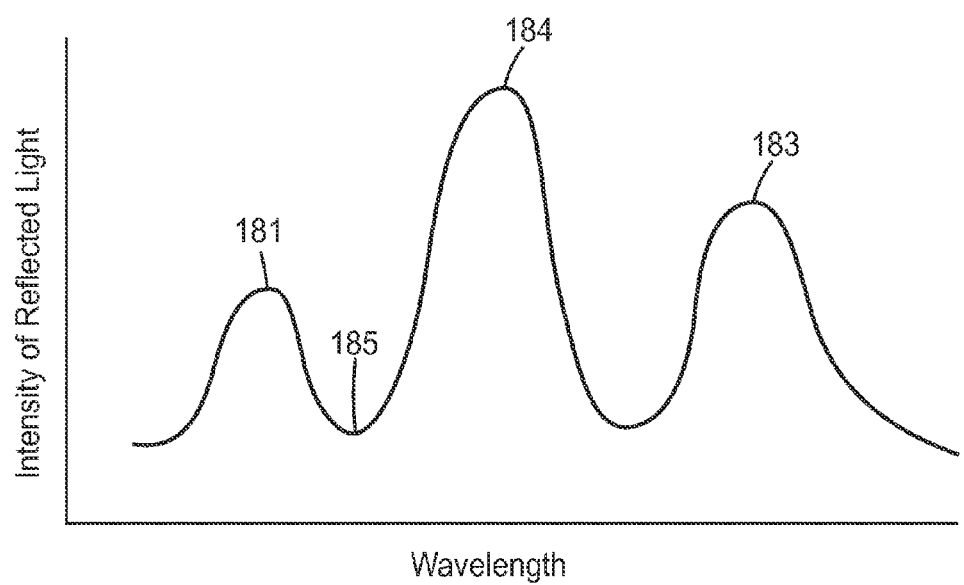
FIG. 2 is a generic representation of a reflectance spectrum exhibited by an exemplary sensing element.

Sensing element 2 (referred to generically, and encompassing configurations 2', 2", etc. mentioned herein) is shown in an exemplary embodiment in FIG. 1. Sensing element 2 is a multilayer structure containing at least an optically responsive layer 230 that is between a reflective layer 240 and a semireflective layer 220, the layers combining to comprise a so-called interference filter exhibiting a reflectance spectrum that may change in the presence of an analyte. Sensing element 2 exhibits a reflectance spectrum of the general type shown in generic representation in FIG. 2 and that comprises one or more peaks (e.g., 181, 183, and 184) and valleys (e.g., 185) at different wavelengths and that may change in the presence of an analyte or upon a change in the concentration of an analyte. For example, the presence of sufficient analyte may cause the peaks and valleys of FIG. 2 to be shifted to higher (longer) wavelengths. The reflectance spectrum exhibited by sensing element 2 may be manifested upon visual inspection as an appearance (e.g., a relatively dominant color, hue, or shade) that may change upon exposure to sufficient analyte. Thus, upon exposure to a sufficient concentration of analyte, sensing element 2 may change in appearance from a first (initial) appearance to a second appearance that is visually distinguishable from the first appearance.

Sensing element 2 may be optically interrogated by exposing sensing element 2 to incoming light rays 40 (as shown in FIG. 1) and observing light reflected from sensing element 2. A dedicated (external) light source is not needed to provide light rays 40 (although one or more dedicated light sources may be so used if desired). Light rays 40 may originate from a single discrete light; or, ambient light (which may originate from several discrete light sources, from a combination of light from direct sources and from reflected light, from sunlight, etc.) may be used as the source of light rays 40.

In embodiments incorporating the design shown in FIG. 1, sensing element 2 comprises in order (optional) substrate 210, semireflective layer 220, optically responsive layer 230, and reflective layer 240. Light rays 40 impinge on and pass through substrate 210. Some portion of light rays 40 may reflect from semireflective layer 220 to emerge from sensing element 2 as light rays 41. Another portion of light rays 40 may pass through semireflective layer 220 and pass through optically responsive layer 230 to encounter reflective layer 240. At least a portion of these light rays may reflect from reflective layer 240, to emerge from sensing element 2 as light rays 42. Light rays 41 and 42 may combine (e.g., by constructively and/or destructively interfering) to collectively provide a reflectance spectrum that may change in the presence of an analyte or upon a change in the concentration of an analyte.

In the exemplary design of FIG. 1, analyte may permeate through reflective layer 240 to enter optically responsive layer 230. This may change the optical properties (e.g., the optical thickness) of at least a portion of layer 230 (e.g., a sublayer of layer 230, as disclosed in detail later herein) such that the reflectance spectrum of light reflected from sensing element 2 may change sufficiently to allow the presence of, and/or the concentration of, an analyte to be detected or monitored. In embodiments incorporating the design shown in FIG. 1, reflective layer 240 is analyte-permeable, and is in fluid communication with optically responsive layer 230. In the design of FIG. 1, semireflective layer 220 may or may not be analyte-permeable. In the exemplary design of FIG. 1, light may pass through substrate 210, so substrate 210 should be optically clear at the wavelengths of interest.

Other designs are possible. For example, semireflective layer 220 may be permeable to an analyte, rather than, or instead of reflective layer 240. Properties of optically responsive layer 230, and, if present, of substrate 210, semireflective layer 220, and/or reflective layer 240, as now discussed in further detail, are understood to be applicable to the making of reflective (e.g., interference-based) sensing elements in general. Those of ordinary skill in the art will readily appreciate that even though the same reference numbers may be used to designate the above-referenced layers in different sensing elements of an array, layers so designated may have the same or different configurations and/or compositions.

Optically responsive layer 230 is defined as a layer comprising an optical thickness (physical thickness multiplied by refractive index) at least a portion of which can change in response to an analyte, such that a reflectance spectrum established by optically responsive layer 230 in combination with a suitable reflective layer 240 and semireflective layer 220 can sufficiently shift (e.g., such that a change in the visual appearance of sensing element 2 can be observed under the ordinary conditions in which sensing element 2 is to be used) upon exposure of sensing element 2 to a level of interest of an analyte of interest. Specifically, optically responsive layer 230, when provided between a suitable reflective layer 240 and semireflective layer 220, exhibits a reflectance spectrum that will shift by at least about 15 nm upon exposure to an atmosphere containing 1000 ppm of styrene, which is a suitable representative organic analyte of interest. This and all other references herein to a shift in reflectance spectrum are with reference to measurements performed according to the procedures outlined in the "Response of Samples to a Test Analyte" section of this disclosure. Optically responsive with respect to layer 230 further means that the total (physical) thickness of layer 230, counting all sublayers thereof, is generally on the order of, or near to, the wavelength of visible light (i.e., is from about 100 nm to about 2000 nm). In various specific embodiments, the total physical thickness of layer 230 may be from about 200 nm to about 1500 nm, from about 400 nm to about 1000 nm, or from about 500 nm to about 800 nm. (All thicknesses listed herein refer to physical thickness rather than optical thickness unless so specified).

Figure 3:
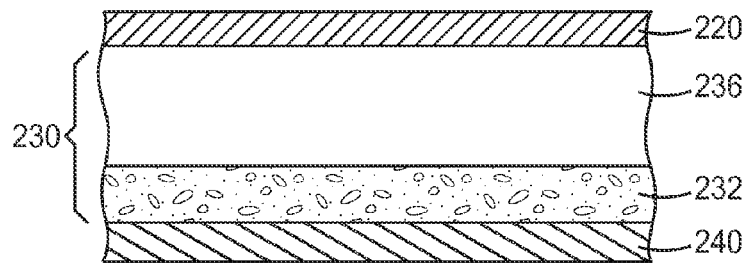
FIG. 3 is a side cross sectional view of a portion of an exemplary sensing element.

Optically responsive layer 230 may comprise at least two sublayers 232 and 236, as shown in FIG. 3. Sublayer 232 is a highly analyte-responsive sublayer as defined herein; sublayer 236 is a minimally analyte-responsive sublayer as defined herein. In various embodiments, the thickness of highly analyte-responsive sublayer 232 may be from about 100 nm to about 800 nm. In various embodiments, the thickness of minimally analyte-responsive sublayer 236 may be from about 700 nm to about 0 nm (that is, in one or more sensing elements 2 of array 1, no minimally analyte-responsive sublayer 236 may be present). In various embodiments, the combined thickness of sublayers 232 and 236 may be from about 200 nm to about 1500 nm. In specific embodiments, the combined thickness of sublayers 232 and 236 may be from about 400 nm to about 1000 nm, or from about 500 nm to about 800 nm.

Array 1 as disclosed herein thus comprises at least two sensing elements 2, at least two of which sensing elements 2' and 2" comprise a significant difference in the thickness of sublayer 232, and/or the thickness of sublayer 236, in the two sensing elements. The difference between the thicknesses of the respective first and second highly analyte-responsive sublayers 232 of two sensing elements is defined as significant if it is at least about 20 nm. For example, for two sensing elements, one with sublayer 232 of 600 nm in thickness and one with sublayer 232 of 580 nm, the difference is significant. Likewise, the difference between the thicknesses of the respective first and second minimally analyte-responsive sublayers 236 of two sensing elements is defined as significant if it is at least about 20 nm. For example, for two sensing elements, one with sublayer 236 of 130 nm thickness, and one with sublayer 236 of 150 nm thickness, the difference is significant. In various embodiments, the difference between the thicknesses of the respective sublayers 236 in two sensing elements is at least about 50 nm, or at least about 100 nm.

Figure 4A:
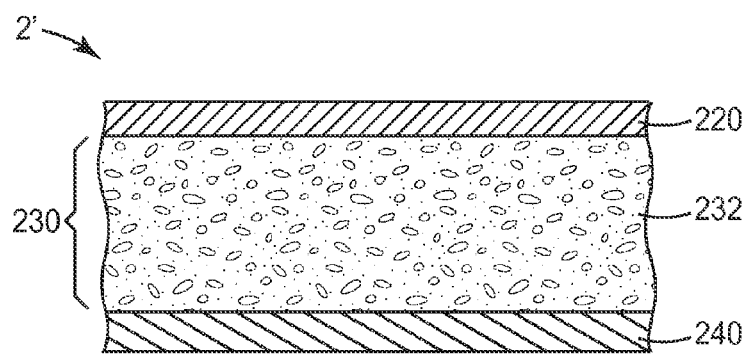
FIGS. 4a, 4b and 4c are side cross sectional views of portions of exemplary sensing elements.
Figure 4B:
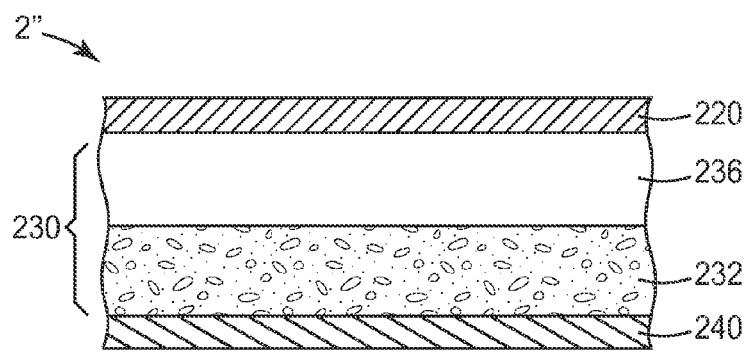
Figure 4C:
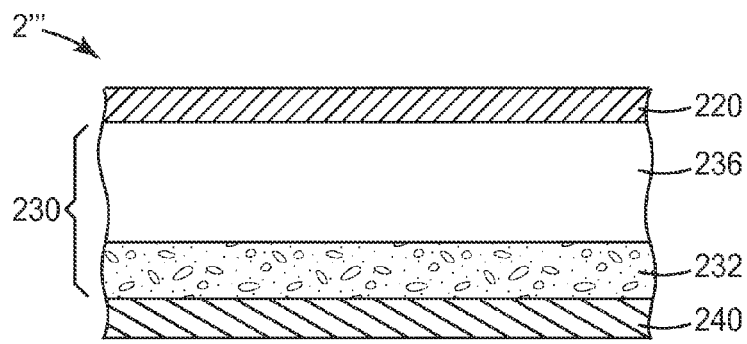

Shown in FIG. 4 in side cross sectional view are three exemplary sensing elements 2', 2", and 2''', two or more of which may be used in combination in array 1. Each of the sensing elements comprises an optically responsive layer 230 of similar (in this context, within about 15%) physical thickness (i.e., so that the three sensing elements each comprise an optically responsive layer 230 of similar optical thickness in the absence of an analyte, e.g. so as to exhibit a similar appearance in the absence of analyte). Optically responsive layer 230 of exemplary sensing element 2' of FIG. 4a is comprised of highly analyte-responsive sublayer 232 with no minimally-responsive sublayer 236 being present. Optically responsive layer 230 of exemplary sensing element 2" of FIG. 4b is comprised of sublayers 232 and 236, of approximately equal thickness. Optically responsive layer 230 of exemplary sensing element 2' of FIG. 4c is comprised of sublayers 232 and 236, in which sublayer 236 is approximately twice the thickness of sublayer 232.

Sublayer 232 is highly responsive to an analyte of interest, which property is achieved by selection of the materials that comprise sublayer 232. In this context, highly responsive to an analyte means that sublayer 232 is sufficiently permeable to the analyte, and that the presence of analyte within sublayer 232 results in sufficient change in the optical thickness of sublayer 232 and hence in the optical thickness of layer 230, that an observable shift in the reflectance spectrum exhibited by sensing element 2 is produced. Specifically, the term highly analyte-responsive means that sublayer 232 is made of a material that, when consisting of a layer of thickness 400-800 nm between a suitable reflective layer and semireflective layer, exhibits a reflectance spectrum that will shift by at least about 15 nm upon exposure to an atmosphere containing 50 ppm of styrene. (As mentioned above, styrene may be used here and elsewhere herein as a useful representative organic analyte, i.e. as a convenient analyte for purposes of characterizing the responsiveness of materials useful in the inventions herein. The use of styrene in this manner in no way should be interpreted as limiting the inventions herein to the monitoring of styrene). In various embodiments, highly analyte-responsive sublayer 232 is made of a material that, when consisting of a layer of thickness 400-800 nm between a suitable reflective layer and semireflective layer, exhibits a reflectance spectrum that, upon exposure to an atmosphere containing 50 ppm of styrene, will shift by at least about 25 nm, at least about 35, or at least about 45 nm.

Sublayer 236 is minimally responsive to the analyte of interest, which property is achieved by selection of the materials that comprise sublayer 236. In this context, minimally responsive to the analyte indicates either that sublayer 236 is not permeable to the analyte to a sufficient extent, and/or the presence of analyte within sublayer 236 does not result in a change in the optical thickness of sublayer 236 that is manifested as a change in the optical properties of layer 230 that results in an observable shift in the reflectance spectrum exhibited by sensing element 2. Specifically, the term minimally analyte-responsive means that sublayer 236 is made of a material that, when consisting of a layer of thickness 400-800 nm between a suitable reflective layer and semireflective layer, exhibits a reflectance spectrum that will shift by no more than about 10 nm upon exposure to an atmosphere containing 20 ppm of styrene. In various embodiments, minimally analyte-responsive sublayer 236 is made of a material that, when consisting of a layer of thickness 400-800 nm between a suitable reflective layer and semireflective layer, exhibits a reflectance spectrum that, upon exposure to an atmosphere containing 20 ppm of styrene, will shift by no more than about 5 nm, about 3 nm, or about 1 nm.

By using an optically responsive layer 230 that comprises a sublayer 232 that comprises a highly analyte-responsive material, and a sublayer 236 that comprises a minimally analyte-responsive material, the response of layer 230 (hence of sensing element 2) to a given level of analyte may be governed by the contributions of both sublayers. For example, a sensing element comprising an optically responsive layer 230 comprising a minimally analyte-responsive sublayer 236 may require a higher concentration of analyte to be present to cause a similar shift in reflectance spectrum, in comparison to a sensing element comprising an optically responsive layer 230 of similar thickness but not comprising a sublayer 236.

For example, in one embodiment sensing element 2 may comprise optically responsive layer 230 comprising highly analyte-responsive sublayer 232 and minimally responsive sublayer 236, configured so that (even though highly analyte-responsive sublayer 232 may be made of a material that, when consisting of a layer of thickness 400-800 nm between a suitable reflective layer and semireflective layer, exhibits a reflectance spectrum that will shift by, e.g., about 100 nm upon exposure to an atmosphere containing 200 ppm of styrene) sensing element 2 exhibits a reflectance spectrum shift of no more than about 40 nm upon exposure to an atmosphere containing 200 ppm of styrene. In further embodiments, such a sensing element may comprise sublayer 232 and sublayer 236 configured such that sensing element 2 exhibits a reflectance spectrum shift of no more than about 30 nm, or of no more than about 20 nm, upon exposure to an atmosphere containing 200 ppm of styrene.

An array comprising multiple individual sensing elements 2, each with a different thickness of sublayer 232 and/or sublayer 236, can thus cover a wide dynamic range of concentration of an analyte of interest, which has advantages as discussed later herein.

Additionally, by using a minimally analyte-responsive sublayer 236 of selected thickness, this thickness being chosen to combine with the selected thickness of sublayer 232 to provide a selected total thickness of optically responsive layer 230, an initial reflectance spectrum (e.g., in the absence of analyte or in the presence of an undetectable level of analyte)

of sensing element 2 can be established (for example, so as to impart sensing element 2 with a particular appearance (e.g., color) upon visual inspection). That is, a sensing element 2 employing sublayers 232 and 236 may be made with an initial appearance similar to that which would be exhibited by a sensing element 2 employing only a highly analyte-responsive material (e.g., not having a sublayer 236), and yet which responds to a different (e.g., higher) concentration of analyte than would a sensing element 2 employing only a highly analyte-responsive material. Thus, in an array comprising multiple individual sensing elements 2, some or all of the individual sensing elements may comprise a similar initial appearance and yet may respond differently to given levels of an analyte, which may have advantages as discussed later herein.

In summary, the use of optically responsive layer 230 comprising sublayers 232 and 236 may allow the selection of the concentration range of analyte to which sensing element 2 may respond, and also may allow an initial color, appearance, etc., of sensing element 2 to be selected. This combination may provide significant advantages.

The use of highly analyte-responsive sublayer 232 in combination with minimally analyte-responsive sublayer 236 may provide additional advantages at least in some embodiments. In particular, reflective sensors of the general type described herein have been known to those of skill in the art to potentially exhibit a phenomenon termed wraparound. In wraparound (upon exposure to a sufficiently high concentration of an analyte), the reflectance spectrum shifts so far that the sensing element changes appearance, back to an appearance similar to the initial appearance exhibited by the sensing element in the absence of analyte. (Further appearance changes may be possible upon exposure to still higher concentrations of analyte). The inventors have surprisingly found that the use of an optically responsive layer 230 comprising a highly analyte-responsive sublayer 232 in combination with a minimally analyte-responsive sublayer 236 can provide a sensing element 2 that is less susceptible to wraparound. In particular embodiments, the properties and thicknesses of sublayers 232 and 236 may be chosen such that sensing element 2 may not exhibit wraparound even in the presence of extremely high levels of analyte. For example, in various embodiments sensing element 2 may not exhibit wraparound even upon exposure to 200, 400, or even 1000 ppm of an organic analyte, e.g., styrene.

In various particular embodiments, such ability to not exhibit wraparound may correspond to the sensing element exhibiting a reflectance spectrum shift of less than about 100 nm, less than about 80 nm, or less than about 60 nm, upon exposure to 200 ppm of an organic analyte, e.g., styrene. In further particular embodiments, such ability to not exhibit wraparound may correspond to the sensing element exhibiting a reflectance spectrum shift of less than about 100 nm, less than about 80 nm, or less than about 60 nm, upon exposure to 400 ppm of an organic analyte, e.g., styrene. In additional particular embodiments, such ability to not exhibit wraparound may correspond to the sensing element exhibiting a reflectance spectrum shift of less than about 100 nm, less than about 80 nm, or less than about 60 nm, upon exposure to 1000 ppm of an organic analyte, e.g., styrene. Thus, an array may be provided in which one or more sensing elements 2 do not exhibit wraparound even in the presence of the highest expected level of organic analyte. Such arrangements may provide advantages, as discussed later herein.

Highly analyte-responsive sublayer 232 can comprise any material that exhibits a sufficiently high response to analyte, e.g., in comparison to the particular minimally analyte-responsive sublayer 236 that it is used in combination with. Thus, sublayer 232 is sufficiently permeable to an analyte of interest, and comprises an optical thickness that can change sufficiently upon exposure to analyte of a chosen concentration to allow the desired functioning of sensing element 2 as described herein. Although not wishing to be bound or limited by any theory or mechanism, the optical thickness of sublayer 232 may change in response to an analyte, for example, via pore-filling (e.g., of a porous material at least partially comprising sublayer 232), which might serve to increase the optical thickness at least by increasing the refractive index. The optical thickness of sublayer 232 may also change in response to an analyte by swelling, which might serve to increase the optical thickness at least by increasing the physical thickness of the layer. Some materials may exhibit a mixture of both responses, may exhibit primarily one response at certain analyte concentrations and another response at other analyte concentrations, and so on.

In some embodiments, sublayer 232 comprises a porous material. In this context, "porous" means that the material comprises internal pores that are at least partially interconnected. Materials may be chosen, for example, with an average (mean) pore size (as characterized, for example, by sorption isotherm procedures) of less than about 100 nm. In various embodiments, materials may be chosen with an average pore size of less than 20 nm, less than about 10 nm, or less than about 2 nm. Sublayer 232 may be homogeneous or heterogeneous, and may, for example, be made from one or more inorganic components, one or more organic components, or a mixture of inorganic and organic components. Representative inorganic materials that may be used in sublayer 232 include metal oxides, metal nitrides, metal oxynitrides and other inorganic materials that can be formed into transparent (and if desired porous) layers of appropriate thickness for producing a suitable optical response.

Porous silica may be an especially desirable inorganic analyte-responsive layer material. Porous silicas may be prepared, for example, using sol-gel processing in which a sol-gel mixture may be converted to a silicate comprising a network of pores within the silica. Plasma chemical vapor deposition may also be employed to generate porous inorganic analyte-responsive materials. This methodology generally involves forming a plasma from gaseous precursors, depositing the plasma on a substrate to form an amorphous random covalent network layer, and then heating the amorphous covalent network layer to form a porous amorphous random covalent network layer. Such methods and materials are described in further detail in International (PCT) Published Patent Application No. U.S. 2008/078281, titled ORGANIC CHEMICAL SENSOR COMPRISING PLASMA-DEPOSITED MICROPOROUS LAYER, AND METHOD OF MAKING AND USING, which is incorporated by reference herein for this purpose.

In some embodiments, optically responsive layer 230 is comprised at least in part of porous organo-silicate materials, herein defined as compositions that are hybrids containing a covalently linked three dimensional silica network (—Si—O—Si—) with some organo-functional groups R, where R is a hydrocarbon or heteroatom substituted hydrocarbon group linked to the silica network by at least one Si—C bond. Such materials and methods of their making are described in further detail in U.S. Provisional Patent Application Ser. No. 61/140,131, titled AMORPHOUS MICROPOROUS ORGANOSILICATE COMPOSITIONS.

In some embodiments, highly analyte-responsive layer 232 is made at least partially from components chosen from the family of materials comprising so-called "polymers of intrinsic microporosity" (hereafter called PIMs). Polymers in this family are described and characterized in, for example, "Polymers of Intrinsic Microporosity (PIMs): Robust, Solution-Processable, Organic Microporous Materials," Budd et al., *Chem. Commun.*, 2004, pp. 230-231; in "Polymers of Intrinsic Microporosity (PIMs)," McKeown et al., *Chem. Eur. J.*, 2005, 11, No. 9, 2610-2620; in U.S. Published Patent Application No. 2006/0246273 to McKeown et al.; and in International (PCT) Published Patent Application No. WO 2005/012397A2 to McKeown et al., all of which are incorporated by reference herein for this purpose.

PIMs can be formulated via the use of any combination of monomers that lead to a very rigid polymer within which there are sufficient structural features to induce a contorted structure. In various embodiments, PIMs can comprise organic macromolecules comprised of generally planar species connected by rigid linkers, said rigid linkers having a point of contortion such that two adjacent planar species connected by the linker are held in non-coplanar orientation. In further embodiments, such materials can comprise organic macromolecules comprised of first generally planar species connected by rigid linkers predominantly to a maximum of two other said first species, said rigid linkers having a point of contortion such that two adjacent first planar species connected by the linker are held in non-coplanar orientation. In various embodiments, such a point of contortion may comprise a spiro group, a bridged ring moiety or a sterically congested single covalent bond around which there is restricted rotation.

In a polymer with such a rigid and contorted structure, the polymer chains are unable to pack together efficiently, thus the polymer possesses intrinsic microporosity. Thus, PIMs have the advantage of possessing microporosity that is not significantly dependent on the thermal history of the material. PIMs thus may offer advantages in terms of being reproducibly manufacturable in large quantities, and in terms of not exhibiting properties that change upon aging, shelf life, etc.

In some embodiments, optically responsive layer 230 is comprised at least in part of porous, highly crosslinked polymeric materials, for example the hypercrosslinked styrenic resins known as "Styrosorbs" (as described for example in V. A. Davankov and P. Tsyurupa, Pure and Appl. Chem., vol. 61, pp. 1881-89 (1989) and in L. D. Belyakova, T. I. Schevchenko, V. A. Davankov and M. P. Tsyurupa, Adv. in Colloid and Interface Sci. vol. 25, pp. 249-66, (1986)), and including those materials available from Purolite (Bala Cynwyd, Pa.) under the trade designation Styrosorb.

For many applications, it may be advantageous that sublayer 232 be hydrophobic. In such embodiments, this may reduce the chance that water vapor (or liquid water) will cause a change in the response of sublayer 232 and interfere with the detection of an analyte, for example, the detection of organic solvent vapors. In some embodiments, highly analyte-responsive sublayer 232 is made of a material that, when provided as a layer of thickness 400-800 nm between a suitable reflective layer and a suitable semireflective layer, exhibits a reflectance spectrum that will shift by no more than 15 nm upon exposure to an atmosphere containing 90% humidity.

Further details and attributes of suitable materials useful for sublayer 232, and methods of making sublayer 232 from such materials, are described in e.g., U.S. Published Patent Application No. 2008/0063874, which is incorporated by reference herein for this purpose.

Minimally analyte-responsive sublayer 236 can be comprised of any material that first, exhibits sufficiently low (including nonexistent and/or nonmeasurable) optical response to an analyte (and to any other substance that might interfere with the sensing of the analyte of interest), in comparison to the particular highly analyte-responsive sublayer 232 that it is used in combination with; that second, is compatible with the processing methods used to produce sublayer 232 (as described later herein); and that third, is optically compatible with sublayer 232. By optically compatible is meant that sublayer 236 is comprised of a material or materials that are sufficiently transparent to light, and that comprise a refractive index that is sufficiently similar to that of sublayer 232, to permit the functioning of sensing element 2. That is, the difference in the refractive index of sublayers 232 and 236 should not be so large as to result in reflections emanating from the interface between sublayers 232 and 236 sufficient to interfere with the functioning of sensing element 2 (e.g., by unacceptably preventing a certain amount of light from reaching highly analyte-responsive sublayer 232, for example in a configuration in which light has to pass through sublayer 236 to reach sublayer 232). Optically compatible with respect to sublayer 236 further means that sublayer 236 does not contain any interfaces, particles, fillers, cavities, etc., that sufficiently reflect, absorb, and/or scatter light so as to unacceptably interfere with the reflectance spectrum of sensing element 2.

Sublayer 236 may be minimally-responsive to analyte due to sublayer 236 being relatively impermeable to the analyte of interest, such that insufficient analyte penetrates into sublayer 236 to cause a response. Thus, in various embodiments sublayer 236 may be comprised of materials with enhanced barrier properties. (In such case, sublayer 236 may preferably be positioned on the opposite side of highly analyte-responsive sublayer 232 from which analyte permeates into sensing element 2, so that analyte can reach sublayer 232). Sublayer 236 thus might be at least partially comprised of a semicrystalline polymeric material (e.g., with a high melting point ($T_m$)), and/or a glassy material (e.g., with a high glass transition temperature ($T_g$)), an inorganic network material (without interconnecting pores), and the like. In some embodiments, sublayer 236 may be at least somewhat permeable to the analyte, but may possess properties such that the presence of analyte (at least up to a certain level) within sublayer 236 does not cause an optical response (e.g., a change in optical thickness of sublayer 236). Thus, materials which have been suitably crosslinked so as to exhibit e.g. little tendency to swell in the presence of certain materials (e.g., water, organic vapors, etc.) may be chosen.

In some embodiments, sublayer 236 comprises a nonporous material. In other embodiments, sublayer 236 comprises a material which is porous, but in which such porosity does not prevent the material from being minimally analyte-responsive. For example, such material may comprise a very low level of porosity and/or may contain pores that are not interconnected (such that the ability of an analyte to permeate into the material is low), or may comprise pores of such large size that an analyte of interest does not condense in the pores until the sensing element is in the presence of a concentration of analyte that is higher than the concentration range of interest.

In various embodiments, sublayer 236 is comprised of a hydrophobic material or materials (which may minimize the chance of water interfering with the detection of certain analytes). In some embodiments, minimally analyte-responsive sublayer 236 is made of a material that, when consisting of a layer of thickness 400-800 nm between a suitable reflective layer and semireflective layer, exhibits a reflectance spectrum that will shift by no more than 15 nm upon exposure to an atmosphere containing 90% humidity.

Particularly in embodiments in which highly analyte-responsive sublayer 232 is deposited onto minimally analyte-responsive sublayer 236 via solution coating (as discussed later), it may be advantageous for the material of sublayer 236 to be resistant to being dissolved, degraded, or otherwise damaged by the solvent used to deposit sublayer 232. In the case that layer 232 comprises an aforementioned polymer of intrinsic microporosity (PIM), it may be useful for sublayer 236 to be resistant to such solvents as are commonly used to solubilize PIMs (e.g., chlorobenzene, chloroform, tetrahydropyran, tetrahydrofuran, and/or mixtures thereof).

In some embodiments, sublayer 236 comprises an uncrosslinked organic polymeric material. In such case, the polymeric material may be chosen to be resistant to absorbing, and/or swelling as a result of absorbing, an analyte or analytes of interest (e.g., organic vapors and the like). Exemplary materials that may be useful include poly(methacrylonitrile) and copolymers and blends thereof. Examples of sensing elements employing certain materials of this type are found in the discussion of samples 1-5. Other polymeric materials that may be suitable candidates (e.g., by virtue of their comprising a relatively high $T_m$ and/or $T_g$ and being relatively hydrophobic) may include for example poly(cyanomethyl acrylate), poly(3,5-dimethyladamantyl crotonate), poly(1-adamantyl acrylate), poly(adamantyl crotonate), poly(pentabromobenzyl acrylate), poly(pentachlorophenyl acrylate), poly(adamantyl methacrylate), poly(4-cyanophenyl methacrylate), poly(3,5-diadamantyl methacrylate), poly(3-tetracyclododecyl methacrylate), poly(2,6-xylenyl methacrylate), poly(methyl β-chloroacrylate), poly[4-(4-biphenylyl)styrene], poly[3-(4-biphenylyl)styrene], poly(2-carboxystyrene), poly(2,4-diisopropylstyrene), poly(2,5-diisopropylstyrene), poly[4-(1-hydroxy-1-methylethyl)styrene], poly[4-(1-hydroxy-1-methylpropyl)styrene], poly(2-hydroxymethylstyrene), poly(4-hydroxymethylstyrene), poly(4-iodostyrene), poly(α-methylstyrene), poly(perfluorostyrene), and poly(4-phenylstyrene).

In some embodiments, sublayer 236 comprises a crosslinked organic polymeric material. Such crosslinking may provide a material with enhanced resistance to absorbing, and/or swelling as result of absorbing, an analyte or analytes of interest, and thus may render a wide variety of materials useful for service in sublayer 236. For example, sublayer 236 may comprise a crosslinked polystyrene material. An example of a sensing element employing such materials is found in the discussion of sample 7. However, any suitable crosslinkable organic polymeric material, of any desired composition or structure, and optionally including additives and the like as are well known in the art, may be used.

In some embodiments, sublayer 236 comprises a crosslinked organic polymeric network achieved by the polymerization and/or reaction of multifunctional monomers, such as the well-known acrylate and methacrylate monomers. Mixtures of such monomers may for example be deposited (either as liquids, or via vapor-condensation methods for example as disclosed in U.S. Pat. No. 5,877,895) and reacted (e.g., radiation-cured) to form a crosslinked layer. Suitable monomers, oligomers, etc. that may be used for such purposes are disclosed for example in U.S. Pat. No. 7,449,146, incorporated by reference herein for this purpose. As mentioned, such layers should be prepared under such conditions so as to achieve properties (e.g., a high degree of crosslinking) that render them suitable to serve as sublayer 236. Other vapor coated organic polymeric materials may be used in sublayer 236, including for example the well-known coatings available from various sources under the trade designation Parylene. Whether crosslinked or uncrosslinked, it may be desirable for sublayer 236 to be hydrophobic, as mentioned previously.

Sublayer 236 may also comprise an inorganic material, e.g., that does not comprise porosity. As discussed above, the refractive index of the inorganic material should be sufficiently similar to that of sublayer 232 to permit the proper functioning of sensing element 2. For example, sublayer 236 may comprise silicon oxide (e.g., deposited by vapor coating). Such an inorganic material may comprise the entire thickness of sublayer 236. Or, sublayer 236 may comprise a barrier sublayer of inorganic material that is adjacent to sublayer 232, with a backing sublayer (e.g., of organic polymeric material) being behind the inorganic barrier sublayer and being present to provide the desired total thickness of sublayer 236. (An example of a sensing element employing such an approach is found in the discussion of sample 6). If the inorganic material is sufficiently impermeable to the analyte, the backing layer may be comprised of any suitable material (e.g., without particular regard to any need to be impermeable to the analyte) since in this configuration it may simply serve as a space filler and thus its barrier properties and/or responsiveness to the analyte may not be a factor.

In various embodiments, sublayer 236 may comprise combinations (e.g., mixtures, blends, composite structures, and the like) of the above-listed materials, and/or multiple layers of such materials.

Sensing element 2 may comprise reflective layer 240. In some embodiments, reflective layer 240 may be deposited (e.g., by various known methods) upon the surface of a previously formed optically responsive layer 230; or, reflective layer 240 may be deposited onto substrate 210 with other layers and/or sublayers of sensing element 2 then being deposited thereon.

Reflective layer 240 may comprise any suitable material that can provide sufficient reflectivity. Suitable materials for the reflective layer may include metals or semi-metals such as aluminum, chromium, gold, nickel, silicon, titanium, platinum, palladium, and silver. Other suitable materials that may be included in the reflective layer may include metal oxides. In some embodiments, the reflective layer may be at least about 90% reflective (i.e., at most about 10% transmissive), and in some embodiments, about 99% reflective (i.e., about 1% transmissive), at a wavelength of about 500 nm.

In some embodiments (e.g., incorporating the design of FIG. 2), reflective layer 240 may advantageously be permeable to an analyte of interest. This may be provided, for example, by forming reflective layer 240 of metal nanoparticles arranged in a morphology which approximates a stack of marbles and through which the analyte can permeate to reach and enter optically responsive layer 230. Layer 240 may be formed by applying a dilute coating solution or suspension of metal nanoparticles to optically responsive layer 230 and allowing the solution or suspension to dry to form permeable reflective layer 240. The metal nanoparticles may be borne in a variety of carriers, including water, and organic solvents (e.g. methanol, heptane, decane, etc.). The metal nanoparticles may also be borne in a polymerizable monomeric binder but desirably such binder is removed from the applied coating (using e.g., solvent extraction or sintering) so as to provide a permeable nanoparticle layer.

Further details and attributes of suitable analyte-permeable materials useful for reflective layer 240, in particular metal nanoparticle materials, are described in e.g., U.S. Published Patent Application No. 2008/0063874, which is incorporated by reference herein for this purpose.

Sensing element 2 may comprise semireflective layer 220. In various embodiments, semireflective layer 220 may be deposited (e.g., by various known methods) upon the surface of a previously formed optically responsive layer 230; or, semireflective layer 220 may be deposited onto substrate 210, with other layers and/or sublayers of sensing element 2 being deposited onto semireflective layer 220 thereafter.

Semireflective layer 220 may comprise a reflectivity that is similar to, or lower than, reflective layer 240. Semireflective layer 220 can comprise any suitable material that can provide appropriate semireflectivity (e.g., when at an appropriate thickness). Suitable materials may include metals or semi-metals such as aluminum, chromium, gold, nickel, silicon, palladium, platinum, titanium and silver. Other suitable materials may include metal oxides.

In various embodiments, semireflective layer 220 may be about 30 to about 70% reflective, or from about 40 to about 60% reflective, at a wavelength of about 500 nm.

In some embodiments semireflective layer 220 may advantageously be permeable to an analyte of interest. Thus, in this case it may be preferable to provide semireflective layer 220 at an appropriate thickness in order to provide appropriate reflectivity while permitting an analyte to permeate through semireflective layer 220 to reach and enter optically responsive layer 230. In some cases, a thickness in the general range of 5-10 nm may be desired (e.g., if semireflective layer 220 is deposited by vapor deposition to form a metal layer). Specific desired thicknesses will depend on the material used to form the layer, the analyte to be detected, and may be configured as necessary.

Further details of suitable semireflective layers and reflective layers, their properties and methods of making, are described for example in U.S. Published Patent Application No. 2008/0063874, incorporated by reference herein for this purpose.

Substrate 210, if present, may be comprised of any suitable material (e.g., glass, plastic, etc.) capable of providing support for the sensing element. In embodiments in which light passes through substrate 210 in order for sensing element 2 to be interrogated, substrate 210 should be optically clear (i.e., should comprise sufficient transparency at the wavelengths of interest) and should not have other properties (e.g., fluorescence) that would unacceptably affect the optical signal. Suitable materials for substrate 210 may include for example the well known polyester family of polymers (e.g., poly(ethylene terephthalate) and poly(ethylene naphthalate)).

Prior to use, sensing elements as disclosed herein may be maintained (e.g. packaged) in an environment substantially free of an analyte of interest. In such an environment, and/or prior to being exposed to an atmospheric concentration of analyte sufficient to cause a response, a sensing element may display a first appearance (e.g., color). Upon being exposed to an atmosphere containing a sufficiently high concentration of an analyte of interest, the reflectance spectrum exhibited by the sensing element may change (e.g., shift by a number of nanometers, typically to a longer wavelength) such that the sensing element undergoes a visually observable change from the first appearance to a second appearance that is different from the first appearance.

The optical response exhibited by the sensing element is typically observable in the visible light range and can be detected by the human eye as a change in appearance. Such a change in appearance may comprise e.g., a change from a first color to a second color, a change in the perceived brightness of the sensing element (e.g., while remaining generally in the same color range), a change from a relatively colorless appearance to a more colorful appearance, a change from a generally uniform appearance to a more nonuniform (e.g., variegated) appearance, and the like. While in some embodiments, it may be desired that array 1 be comprised of sensing elements 2 that all comprise a similar first appearance and a similar second appearance, in other embodiments, different sensing elements of array 1 may comprise a different first appearance or second appearance from that of other sensing elements of array 1. While optical interrogation thus may in some embodiments be performed by visual inspection (e.g., by a person), in some embodiments other interrogation methods may be used, including for example an external interrogation device such as a spectrophotometer, photo-detector, charge coupled device, photodiode, digital camera, and the like. Use of such optoelectronic methods for interrogation of sensing element 2 is discussed in U.S. patent application Ser. No. 61/164,496, herein incorporated by reference for this purpose.

Further details of the components and construction of some types of sensing elements 2 is discussed in the copending U.S. Provisional Patent Application Ser. No. 61/180,483 titled MULTILAYER COLORIMETRIC SENSORS, filed 22 May 2009, which is herein incorporated by reference.

An array comprising multiple sensing elements, as disclosed herein, may be used to detect and/or monitor one or more analytes of interest, over a wider concentration range than may be possible with a single sensing element. Such an analyte may comprise a vapor or gas that may be present in an environment (often, an air atmosphere) that is desired to be monitored. In some embodiments, the analyte is an organic vapor (e.g., a volatile organic compound). In specific embodiments, the analyte is a high boiling organic compound, defined herein as an organic compound having a boiling point of 100° C. or greater. Representative organic analytes may include substituted or unsubstituted carbon compounds including alkanes, cycloalkanes, aromatic compounds, alcohols, aldehydes, ethers, esters, ketones, halocarbons, amines, organic acids, cyanates, thiols, nitrates, and nitriles, for example n-octane, cyclohexane, methyl ethyl ketone, acetone, ethyl acetate, carbon disulfide, carbon tetrachloride, benzene, toluene, styrene, xylenes, chloroform, tetrahydrofuran, methanol, ethanol, isopropyl alcohol, n-butyl alcohol, t-butyl alcohol, 2-ethoxyethanol, acetic acid, 2-aminopyridine, ethylene glycol monomethyl ether, toluene-2,4-diisocyanate, nitromethane, acetonitrile, and the like. (Of these, styrene may serve as a representative organic analyte useful in characterizing the response of sensing element 2, optically responsive layer 230, highly analyte-responsive sublayer 232, and/or minimally analyte-responsive sublayer 236, as discussed herein. Others may also serve).

In some cases array 1 may be used to detect water (e.g., as a humidity sensor). In other embodiments, some or all of sensing elements 2 of array 1 may be designed (e.g., through selection of hydrophobic materials for sublayers 232 and/or 236) to have minimal response to the presence of water.

As discussed earlier herein, an array as described herein can provide an expanded dynamic range of response to concentrations (in a monitored atmosphere) of a given analyte of interest. That is, several sensing elements can be provided, each of which optically responds to a different concentration range of an analyte of interest. (The dynamic range of the individual sensing elements may at least partially overlap, as discussed herein). Thus, for example, a first sensing element might optically respond to 20 ppm of an analyte of interest, a second sensing element might respond to 40 ppm, a third might respond to 80 ppm, a fourth to 100 ppm and so on. Also as mentioned, the array can comprise multiple sensing elements each of which exhibit a similar initial color or appearance (in the absence of analyte or in the presence of an concentration of analyte undetectable by that sensing element).

In some embodiments, array 1 comprises at least one sensing element 2 that may not undergo the aforementioned wraparound phenomenon in the presence of the highest expected analyte concentration to which the array is expected to be exposed. The presence of at least one such wraparound-resistant sensing element thus may ensure that even in the event of exposure to a very high analyte concentration (e.g., the highest expected to be encountered in the particular use) the enhanced dynamic range array may allow successful detection of the analyte.

In additional embodiments, the sensing elements may be designed such that there is overlap between the dynamic ranges of at least two of the elements. That is, at least two sensing elements, a first designed to optically respond at a lower analyte concentration and a second designed to optically respond at a higher analyte concentration, and with the first one exhibiting wraparound at a particular analyte concentration, may be provided. The second sensing element may be designed so that it exhibits an appearance change (e.g., from a first color to a second color) at an analyte concentration lower than the particular analyte concentration which would trigger wraparound of the first sensing element, such that the dynamic range of the second sensing element overlaps with that of the first sensing element. (The second sensing element may be one that does not exhibit wraparound even at the highest anticipated analyte levels; or it may be an "intermediate-sensitivity" sensing element which still may exhibit wraparound at a certain level of analyte).

The methods described herein thus may provide a fundamental advance in the art of using reflective (e.g., interference-based) sensing elements. The use of an array of sensing elements, each of which may respond to a different level of analyte, enables the production of devices with (due to the collective response of the sensing elements therein) a very wide dynamic range. Furthermore, the presence of at least one sensing element that may not exhibit wraparound at the highest expected analyte level, and the further presence of the above-mentioned overlap between the dynamic range of at least some of the pairs of sensing elements, thus enables a very advantageous mode of sensing.

For example, an array may be provided in which the individual sensing elements all have a similar first (initial) appearance (e.g., color) in the absence of detectable levels of analyte. Upon exposure to a "lower" level of an analyte of interest, at least a first sensing element (e.g., one which is capable of responding to the lowest level of analyte) may change to a second appearance. Upon exposure to an intermediate level of analyte, a second sensing element may change to the second appearance, prior to the first sensing element exhibiting wraparound and hence changing back to the first appearance. Upon exposure to a higher level of analyte, yet a third sensing element may change to a second appearance, prior to the second sensing element exhibiting wraparound and hence changing back to the first appearance. Upon the exposure of the array to the highest expected level of analyte, at least one sensing element which has been designed not to exhibit wraparound upon exposure to such levels of analyte, may remain at the second appearance. Thus, an array may be provided in which, in the presence of any detectable level of analyte, at least one of the sensing elements will exhibit the second appearance. A user of such an array may thus appreciate that exhibition of the second appearance by at least one of the sensing elements of the array (regardless of the appearance of any other sensing elements of the array), and/or the presence of a difference in the appearance between any two sensing elements of the array, may indicate the presence of some detectable level of the analyte. Such an array may also be used to provide a semiquantitative or quantitative indication of the concentration of an analyte of interest present in a monitored atmosphere.

The particular level of analyte at which such change in appearance of the various sensing elements occurs can be varied by the particular design of the individual sensing elements, depending on the particular analyte of interest, workplace requirements for a particular analyte, and so on. Multiple sensing elements can be provided with the above-described overlap being present between several different sensing elements.

The optical response of an exemplary array 1 comprising a first exemplary sensing element 2' and a second exemplary sensing element 2" (which do not necessarily have to correspond to, and/or be the exact design of, exemplary sensing elements 2' and 2" described with reference to FIGS. 4a and 4b) is generically illustrated in FIG. 5. With reference to FIG. 5, in the absence of a detectable level of analyte both sensing elements may remain in a first condition (e.g., appearance). Upon exposure to a first, lower level of analyte, the first sensing element 2' may change to a second condition, with the second sensing element 2" remaining in the first condition. Upon exposure to an intermediate level of analyte (that is higher than the first, lower level), the second sensing element 2" may change to the second condition with the first sensing element 2' remaining in the second condition (with the array thus exhibiting the above-mentioned overlap in dynamic range). Upon exposure to a higher level of analyte (that is higher than the intermediate level), the first sensing element 2' may exhibit wraparound and return to the first condition; however, the second sensing element 2" may not exhibit wraparound and thus remains in the second condition. The presence of a second condition, of either of the two sensing elements, thus indicates that a detectable level of analyte is present.

This simple example thus illustrates the enhancement in dynamic range, reliability and/or accuracy, that can be provided by the methods herein. The use of additional sensing elements (beyond two), the particular design of the sensing elements, and so on, can provide further enhancements. While in the examples presented herein, the first and second conditions correspond to first and second appearances, if monitored visually, or first and second wavelength spectra (with a shift therebetween), if monitored via optoelectronic methods, these general methods may be broadly applicable, for example, to conditions that are measured by other means.

In further extensions of these methods, other features may be provided. For example, one or more reference elements (e.g., of unchanging appearance) may be provided as an aid to the user in discerning color changes. Such a reference element, for example, may comprise a colored or painted material or area or may comprise a sensing element (e.g., of the general type described herein) that is designed so as to not exhibit an optical response to a particular (e.g., low) concentration of an analyte. It should also be noted that the herein-described use of an array with multiple sensing elements with a similar initial appearance may usefully provide a "self-referencing" feature of the array such that separately supplied reference elements may not be needed. Regardless of how achieved, in some embodiments array 1 may be arranged such that, in the presence of a detectable level of analyte, a user may perceive a difference in appearance between at least any two individual sensing elements of array 1 (e.g., instead of, or in addition to, perceiving that the appearance of an individual sensing element is now different than it was previously).

Arrays described herein, and methods of using, may be useful in connection with a personal respiratory protection device (e.g., a respirator, such as might contain a filter element, sorbent media, etc., for removal of certain substances from an atmosphere), for example as an end of service life indicator (ESLI) that can monitor an atmosphere comprising an air stream that has passed at least partially through a filter element, sorbent media, etc. present in the respiratory protection device, and that may indicate for example that the filter element, sorbent media, etc. may be exhausting its capacity to remove the analyte from the air stream. In such uses, it may be desirable to detect an analyte of interest (e.g., in an airstream that has passed or is passing through a filter element or sorbent bed), for example at a so-called Occupational Exposure Limit (OEL) of concentration. However, such personal respiratory devices may in some cases be used in atmospheres that contain the analyte at levels of up to 10 times, or even 50 times, the OEL. Thus, the use of a single sensing element which might detect a low level of analyte, but might exhibit wraparound in the event of exposure to a higher level of analyte (e.g., in the event of breakthrough of the analyte upon the saturation or exhaustion of the sorbent media), may not be as advantageous as the use of an array comprising multiple sensing elements. That is, the ability to detect low levels of analyte is preserved, and yet the ability to detect high levels of analyte is also enabled.

Referring to FIG. 6, in some embodiments a personal respirator 101 in which array 1 may find use includes a face mask 102 on which is mounted a pair of replaceable air purifying respirator cartridges 103. The cartridges 103 each serve as enclosures for a sorbent material (e.g., activated carbon) not shown in FIG. 6. The front cover 104 of each cartridge 103 includes a plurality of openings 105 that serve as gas inlets, permitting ambient air from the external environment to flow into cartridge 103, through the sorbent material and thence through a passage (not labeled in FIG. 6) that serves as a gas outlet from cartridge 103 and an inlet to face mask 102. Exhaled air exits respirator 101 through exhalation valve 109. The indicator may be used in a variety of respiratory protective devices. For example, the indicator may also be deployed in a single cartridge respirator or a powered air-purifying respirator. The sidewall 106 in each cartridge 103 may include one or more transparent viewing ports 107 through which sensing elements 2 of array 1 can be seen. Or, the entirety of sidewall 106, or the entirety of cartridge 103, may be transparent (e.g., comprised of optically clear plastic material).

Figure 7:
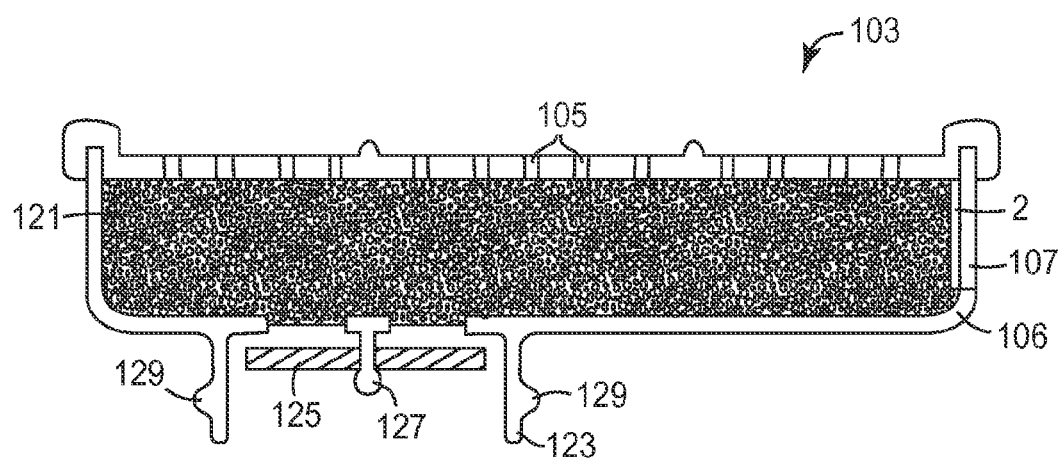
FIG. 7 is a side cross sectional view of the replaceable cartridge for use in the respirator of FIG. 6.
Figure 8:
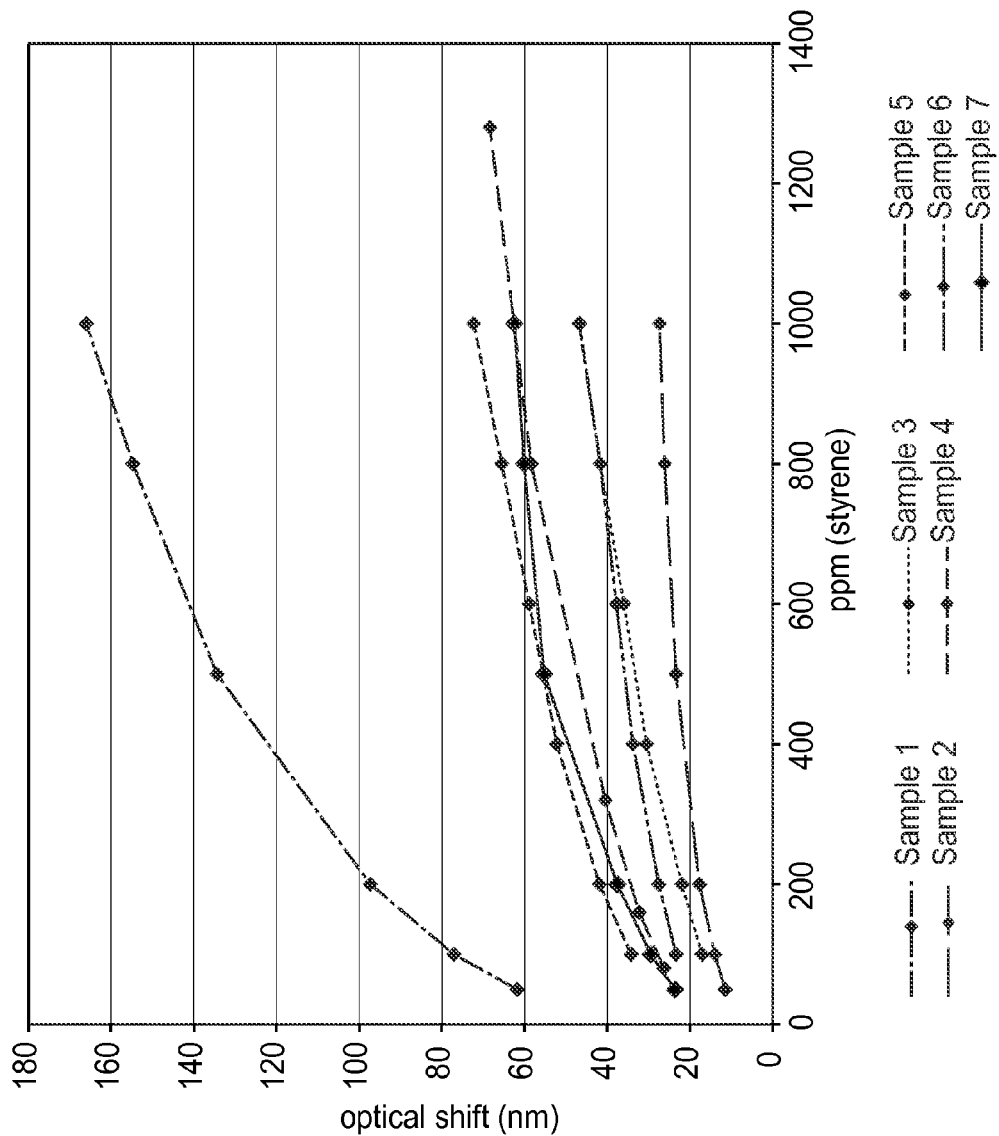
FIG. 8 is a plot of experimentally obtained data showing the observed wavelength shift upon exposure to various concentrations of a test analyte, for various sensing elements.

FIG. 7 is a side cross sectional view of respirator cartridge 103. If desired, the openings 105 could be sealed until use using for example a removable cover (not shown in FIG. 6 and FIG. 7) that would be removed before use. A bed of sorbent material 121 absorbs or adsorbs at least a portion of one or more analytes (e.g., organic vapors) of interest passing from the openings 105 to outlet 123. One-way inhalation valve 125 mounted on post 127 prevents exhaled air from entering cartridge 103. A threaded or preferably bayoneted connector or connectors 129 can be used to removably couple cartridge 103 to mask 102. Sidewall 106 may include one or more transparent viewing ports 107 as referred to above. Viewing port 107 may comprise an optically clear portion of sidewall 106; or, viewing port 107 may comprise an opening in sidewall 106 with one or more sensing elements 2 mounted therein in such a way as to occlude port 107 (e.g., with substrate 210 of sensing element 2 serving as an occlusive barrier). Port 107 permits light (e.g., ambient light) to strike sensing elements 2 and permits light reflected therefrom to exit cartridge 103. If desired, a removable or replaceable shield or other covering (not shown in FIG. 7) may optionally be used to protect port 107 from paint or foam overspray, dust, or other obscuration. In some uses, cartridges 103 would be removed and replaced with fresh cartridges 103 when a visibly discernible change in the appearance of at least one sensing element 2 (e.g., a change in appearance) indicates that a level of analyte is present in the airstream (downstream of sorbent material 121) that indicative of a need to replace cartridges 103 (e.g., that sorbent material 121 has become equilibrated with the analyte at the conditions of exposure). Sensing elements 2 may be placed in any suitable configuration within cartridge 103 and with respect to sorbent material 121, as long as the sensing elements are positioned so as to adequately report the concentration of analyte in the airstream that is passing through, or has passed through, sorbent material 121. In some embodiments, a sensing element 2 of the general type shown in FIG. 1 may be preferred (e.g., using an analyte-permeable reflective layer 240). In such case, sensing elements 2 may be positioned with analyte-permeable reflective layer 240 facing inward toward the interior of cartridge 103 (so that analyte in the airstream within cartridge 103 can readily penetrate sensing element 2) and with (optically clear) substrate 210 facing outward (e.g., positioned adjacent or in contact with an optically clear material that comprises transparent viewing port 107) so that sensing elements 2 can be optically interrogated. In some embodiments, sensing elements 2 may be oriented with their plane generally parallel to the air flow path through cartridge 103 and optionally with their length extending the full length of the air flow path, so that an appearance change (e.g., a color change) "front" visible in sensing element 2 might advance with the flow of analyte through the sorbent material 21. Other configurations are possible. For example, sensing elements 2 could be placed toward the end of the flow path (e.g., downstream of sorbent material 121).

Sensing elements 2 of array 1 may be held in place on cartridge 103 (e.g., within the interior of cartridge 103) by any suitable method or device. For example, each individual sensing element 2 may be held in place (e.g., against an interior surface of transparent viewing port 107 of side wall 106) by pressure exerted by sorbent material 121. Or, sensing element 2 may be attached (to sidewall 106, or to some other portion of cartridge 103) via one or more mechanical attachment devices such as a screw, nail, clamp, clip, bracket, hook and loop connector, and the like. Or sensor 99 may be attached by solvent welding, ultrasonic welding, liquid adhesive (e.g., radiation-cure adhesive, cyanoacrylate, epoxy, and the like). A molded slot, housing, or other support structure may be provided within cartridge 103 to hold sensing element 2.

In some embodiments, sensing element 2 may be held in place via an optically clear double faced pressure-sensitive adhesive. In specific embodiments, such an adhesive may be provided as a layer between at least a portion of sensing element 2 (e.g., in contact with optically clear substrate 210) and at least a portion of transparent viewing port 107. In such case, optical interrogation of sensing element 2 may occur via light that is transmitted through transparent viewing port 107, the optically clear adhesive, and optically clear substrate 210. In some embodiments, one or more of the sensing elements may be provided on (e.g., laminated to) an optically clear carrier (e.g., a section of glass, transparent plastic, etc.) that may be appreciably thicker than optically clear substrate 210 and that may be positioned adjacent, and/or attached to, a portion of transparent viewing port 107.

Sensing elements 2 of array 1 may be arranged near each other or may be separated (e.g., on different sidewalls 106 of cartridge 103, viewed through different viewing ports 107). Sensing elements 2 may be arranged linearly, in a grid, etc., as desired. If desired, sensing elements 2 may be arranged to enhance the ability of a user to perceive a difference in appearance between the sensing elements. (For example, sensing elements may be juxtaposed in close proximity, one sensing element may surround another sensing element, etc.).

Further details of methods and devices that may be used in the incorporation of herein-disclosed sensing elements and/or arrays into respirator cartridges are discussed in U.S. patent application Ser. No. 12/470,865, (titled FILTER CARTRIDGE HAVING COVER FOR MASKING SERVICE LIFE INDICATOR and now issued as U.S. Pat. No. 8,336,543); Ser. No. 12/470,890, (titled FILTER CARTRIDGE HAVING LOCATION-REGISTERED VIEW WINDOW FOR END-OF-SERVICE-LIFE INDICATOR and now issued as U.S. Pat. No. 8,225,782); and Ser. No. 12/470,920, (titled FILTER CARTRIDGE HAVING CONE OF VISIBILITY FOR END-OF-SERVICE-LIFE-INDICATOR (ESLI) and now issued as U.S. Pat. No. 8,365,723); all filed 22 May 2009, and all of which are all incorporated by reference herein.

In other embodiments a personal respirator 101 in which array 1 may find use comprises a disposable mask (e.g. of the general type shown e.g. in U.S. Pat. No. 6,234,171), modified to include array 1 comprising sensing elements 2. In such embodiments, the mask may have a generally cup-shaped shell or respirator body comprising a layer of sorbent material. The mask may include a transparent viewing port through which sensing elements 2 (which are downstream of the sorbent material) can be observed. Further details regarding the construction of such a respirator will be familiar to those skilled in the art.

Array 1 comprising sensing elements 2 may also used in personal monitors and/or area monitors, such as those discussed in U.S. Provisional Patent Application Ser. No. 61/148,228, herein incorporated by reference for this purpose.

EXAMPLES

All reagents and materials used in these examples were obtained from Sigma-Aldrich, St. Louis, Mo., unless otherwise noted.

Preparation of TFTN-PIM 1

In a 2.0 L three-neck round bottomed flask, 33.4357 g of 3,3,3',3'-tetramethyl-1,1'-spirobisindane-5,5',6,6'-tetrol (tetrol) and 19.8016 g of tetrafluoroterephthalonitrile (TFTN) were dissolved in 900 mL of anhydrous N,N-dimethyl formamide (DMF). The solution was stirred with a mechanical stirrer, and nitrogen was bubbled through the solution for one hour. To this solution was added 81.4491 g of potassium carbonate (EMD Chemicals, Gibbstown, N.J.). The flask was placed in an oil bath at 68° C. The mixture was stirred at this elevated temperature under a nitrogen atmosphere for 65 hours. The polymerization mixture was poured into 9.0 L of water. The precipitate formed was isolated by vacuum filtration and washed with 600 mL of MeOH (VWR, West Chester, Pa.). The isolated material was spread out in a pan and allowed to air dry overnight. The solid was placed in a jar and dried under vacuum at 68° C. for 4 hours. The resulting yellow powder was dissolved in 450 mL of THF (EMD). This solution was poured slowly into 9.0 L of methanol. The precipitate formed was isolated by vacuum filtration. The isolated material was spread out in a pan and allowed to air dry overnight. The solid was placed in a jar and dried under vacuum at 68° C. for 4 hours. The precipitation in methanol was performed one more time. The resulting dried, bright yellow polymer weighed 42.80 g. Analysis of the polymer by GPC using light scattering detection showed the material to have a $M_n$ of approximately 30,900.

Preparation of TFTN-PIM 2

In a 2.0 L three-neck round bottomed flask, 33.4365 g of tetrol and 19.8011 g of TFTN were dissolved in 900 ml of anhydrous DMF. The solution was stirred with a mechanical stirrer, and nitrogen was bubbled through the solution for one hour. To this solution was added 81.4480 g of potassium carbonate. The flask was placed in an oil bath at 68° C. The mixture was stirred at this elevated temperature under a nitrogen atmosphere for 67.5 hours. The polymerization mixture was poured into 9.0 L of water. The precipitate formed was isolated by vacuum filtration and washed with 600 mL of MeOH. The isolated material was spread out in a pan and allowed to air dry overnight. The solid was placed in a jar and dried under vacuum at 68° C. for 4 hours. The resulting yellow powder was dissolved in 450 mL of THF. This solution was poured slowly into 9.0 L of methanol. The precipitate formed was isolated by vacuum filtration. The isolated material was spread out in a pan and allowed to air dry overnight. The solid was placed in a jar and dried under vacuum at 68° C. for 4 hours. The precipitation in methanol was performed one more time. The resulting dried, bright yellow polymer weighed 43.22 g. Analysis of the polymer by GPC using light scattering detection showed the material to have a $M_n$ of approximately 35,800.

Preparation of TFTN-PIM 3

In a 2.0 L three-neck round bottomed flask, 33.4366 g of 3,3,3',3'-tetramethyl-1,1'-spirobisindane-5,5',6,6'-tetrol (tetrol) and 19.8008 g of tetrafluoroterephthalonitrile (TFTN) were dissolved in 900 mL of anhydrous N,N-dimethyl formamide (DMF). The solution was stirred with a mechanical stirrer, and nitrogen was bubbled through the solution for one hour. To this solution was added 81.4480 g of potassium carbonate (EMD Chemicals, Gibbstown, N.J.). The flask was placed in an oil bath at 68° C. The mixture was stirred at this elevated temperature under a nitrogen atmosphere for 67.5 hours. The polymerization mixture was poured into 9.0 L of water. The precipitate formed was isolated by vacuum filtration and washed with 600 mL of MeOH (VWR, West Whester, Pa.). The isolated material was spread out in a pan and allowed to air dry overnight. The solid was placed in a jar and dried under vacuum at 68° C. for 4 hours. The resulting yellow powder was dissolved in 450 mL of THF (EMD). This solution was poured slowly into 9.0 L of methanol. The precipitate formed was isolated by vacuum filtration. The isolated material was spread out in a pan and allowed to air dry overnight. The solid was placed in a jar and dried under vacuum at 68° C. for 4 hours. The precipitation in methanol was performed one more time. The resulting dried, bright yellow polymer weighed 42.90 g. Analysis of the polymer by GPC using light scattering detection showed the material to have a $M_n$ of approximately 40,000.

Preparation of Sample 1

A metalized polyethylene terephthalate (PET) substrate was prepared by evaporatively depositing a 10 nm-thick Ni metal layer onto Melinex ST505 clear PET (Dupont Teijin). A 4% by weight solution of TFTN-PIM 1 in chlorobenzene (Alfa Aesar, Ward Hill, Mass.) was prepared and deposited onto the Ni-coated PET by slot die coating, to a thickness of approximately 600 nm. A silver nanoparticle layer was deposited by slot die coating onto the TFTN-PIM layer using 100 g of stock nanosilver suspension (DGP-40LT-15C from Advanced Nanoproducts, Korea, 40% by weight silver) diluted with 150 g of 1-methoxy-2-propanol (Dow Chemical, Midland, Mich.). After deposition, the overall sensor construction was heated at 150° C. for 1 hour to sinter the silver nanoparticles.

Preparation of Sample 2

A Ni-coated PET substrate was prepared as described in Preparation of Sample 1. A 6% by weight solution of poly (methacrylonitrile) (PMAN) (Scientific Polymer Products, Inc., Ontario, N.Y., $M_w$ approximately 20,000) in nitromethane (EMD) was prepared, and the solution was coated onto the Ni-PET substrate by spin coating at 2100 rpm for 2 minutes using a WS-400B-8NPP-Lite Single Wafer spin processor manufactured by Laurell Technologies, Corp., North Wales, Pa. A 2% by weight solution of TFTN-PIM 2 in chlorobenzene was prepared and coated on top of the PMAN layer by spin coating at 1500 rpm. A 0.5 g quantity of the commercially available silver nanoparticle suspension described in the Preparation of Sample 1 was diluted with 1 mL of methanol. This silver nanoparticle suspension was coated on top of the TFTN-PIM layer by spin coating at 1000 rpm. After deposition, the overall sensor construction was heated at 150° C. for 1 hour to sinter the silver nanoparticles. The overall thickness of the PMAN/TFTN-PIM was approximately 600 nm with the TFTN-PIM layer being approximately 100 nm thick.

Preparation of Sample 3

A Ni-coated PET substrate was prepared as described in Preparation of Sample 1. A 6% by weight solution of PMAN in cyclohexanone (EMD) was prepared, and the solution was coated onto the Ni-PET substrate by spin coating at 1100 rpm. A 3% by weight solution of TFTN-PIM 2 in chlorobenzene was prepared and coated on top of the PMAN layer by spin coating at 1500 rpm. A 0.5 g quantity of the commercially available silver nanoparticle suspension described in the Preparation of Sample 1 was diluted with 1 mL of methanol. This silver nanoparticle suspension was coated on top of the TFTN-PIM layer by spin coating at 1000 rpm. After deposition, the overall sensor construction was heated at 150° C. for 1 hour to sinter the silver nanoparticles. The overall thickness of the PMAN/TFTN-PIM was approximately 600 nm with the TFTN-PIM layer being approximately 200 nm thick.

Preparation of Sample 4

A Ni-coated PET substrate was prepared as described in Preparation of Sample 1. A 6% by weight solution of PMAN in cyclohexanone was prepared, and the solution was coated onto the Ni-PET substrate by spin coating at 1500 rpm. A 4% by weight solution of TFTN-PIM 2 in chlorobenzene was prepared and coated on top of the PMAN layer by spin coating at 3000 rpm. A 0.5 g quantity of the commercially available silver nanoparticle suspension described in the Preparation of Sample 1 was diluted with 1 mL of methanol. This silver nanoparticle suspension was coated on top of the TFTN-PIM layer by spin coating at 1000 rpm. After deposition, the overall sensor construction was heated at 150° C. for 1 hour to sinter the silver nanoparticles. The overall thickness of the PMAN/TFTN-PIM was approximately 600 nm with the TFTN-PIM layer being approximately 250 nm thick.

Preparation of Sample 5

A Ni-coated PET substrate was prepared as described in Preparation of Sample 1. A 6% by weight solution of PMAN in cyclohexanone was prepared, and the solution was coated onto the Ni-PET substrate by coating at 1900 rpm. A 4% by weight solution of TFTN-PIM 2 in chlorobenzene was prepared and spin coated on top of the PMAN layer by spin coating at 2000 rpm. A 0.5 g quantity of the commercially available silver nanoparticle suspension described in the Preparation of Sample 1 was diluted with 1 mL of methanol. This silver nanoparticle suspension was coated on top of the TFTN-PIM layer by spin coating at 1000 rpm. After deposition, the overall sensor construction was heated at 150° C. for 1 hour to sinter the silver nanoparticles. The overall thickness of the PMAN/TFTN-PIM was approximately 600 nm with the TFTN-PIM layer being approximately 300 nm thick.

Preparation of Sample 6

A Ni-coated PET substrate was prepared as described in Preparation of Sample 1. A 10% by weight solution of poly (vinylidene chloride-co-acrylonitrile-co-methyl methacrylate) (Sigma-Aldrich, $M_w$ approximately 13,000, $M_n$ approximately 84,000) (PVnCl) in cyclohexanone was prepared, and the solution was coated onto the Ni-PET substrate by spin coating at 1500 rpm. A 500 angstrom layer of $SiO_x$ was evaporatively deposited on top of the PVnCl layer. A 4% by weight solution of TFTN-PIM 2 in chlorobenzene was prepared and coated on top of the $SiO_x$ layer by spin coating at 3000 rpm. A 0.5 g quantity of the commercially available silver nanoparticle suspension described in the Preparation of Sample 1 was diluted with 1 mL of methanol. This silver nanoparticle suspension was coated on top of the TFTN-PIM layer by spin coating at 1000 rpm. After deposition, the overall sensor construction was heated at 150° C. for 1 hour to sinter the silver nanoparticles. The overall thickness of the PVnCl/$SiO_x$/TFTN-PIM was approximately 600 nm with the TFTN-PIM layer being approximately 250 nm thick.

Preparation of Sample 7

A Ni-coated PET substrate was prepared as described in Preparation of Sample 1. A 7% by weight solution of polystyrene (Sigma-Aldrich, $M_w$ approximately 280,000) (PSt) in toluene was prepared, and the solution was coated onto the Ni-PET substrate by spin coating at 2500 rpm. The sample was placed under a germicidal lamp and irradiated for 18 hours. A 4% by weight solution of TFTN-PIM 2 in chlorobenzene was prepared and coated on top of the crosslinked PSt layer by spin coating at 3000 rpm. A 0.5 g quantity of the commercially available silver nanoparticle suspension described in the Preparation of Sample 1 was diluted with 1 mL of methanol. This silver nanoparticle suspension was coated on top of the TFTN-PIM layer by spin coating at 1000 rpm. After deposition, the overall sensor construction was heated at 150° C. for 1 hour to sinter the silver nanoparticles. The overall thickness of the PSt/TFTN-PIM was approximately 600 nm with the TFTN-PIM layer being approximately 250 nm thick.

Preparation of Sample 8

A Ni-coated PET substrate was prepared as described for Sample 1. The TFTN-PIM-3 polymer was dissolved at 4% concentration in chlorobenzene and then deposited onto the metallized PET as described for Sample 1. A silver nanoparticle layer was then deposited onto the TFTN-PIM-3 layer as described for Sample 1.

Preparation of Sample 9

A sample was prepared as described above in Preparation of Sample 4.

Response of Samples 1-7 to a Test Analyte

A simple flow-through custom built delivery system was used to deliver known concentrations of a test analyte (styrene) to the sensing element for measurement. Teflon tubing was used throughout the delivery system. Liquid styrene (Alfa Aesar, 99%, Prod # A18481) was delivered onto a heated platen at a specified flow rate by way of a Harvard Apparatus syringe pump. The platen was located in a 500-mL round bottom flask through which 20 L/min dry air (relative humidity less than about 5%) flow was maintained. The concentration of styrene in the gaseous stream was calibrated by use of an infrared spectrometer (available under the designation Miran Sapphire from ThermoElectron of Waltham, Mass.). The gaseous styrene stream was introduced into a sample chamber (held at room temperature) containing the sensing element sample.

In this manner various individual sensing element samples were sequentially exposed to gaseous streams containing styrene in a concentration range of from 50 to 1300 parts per million. The length of exposure of each sample to a specific concentration of styrene was typically around 50-60 minutes. During the exposure, the sample was optically interrogated via a spectrometer (available from Ocean Optics under the trade designation USB 2000), used with an LS-1 tungsten-halogen lamp as light source, and with a fiber optic reflection probe, and the wavelength spectrum (e.g., similar to that generically shown in FIG. 3) was recorded. For each exposure level, the wavelength shift (measured as the shift in nanometers of a peak (typically a peak with a maxima at approximately 570 nm wavelength)) was recorded (relative to the initial peak location in the absence of analyte). The results of this testing for samples 1-7 are plotted in FIG. 5.

Individual samples 1-7 all exhibited a similar initial appearance (green in color) when viewed from a similar viewing angle, prior to their exposure to the test analyte. Generally with these samples, a wavelength shift (as measured above) of approximately 25 nm was associated with a visually observable change of the appearance of the sensing element from green to red. Thus, sample 1 might be expected to change from green to red when exposed to an atmosphere containing around 20 ppm styrene, sample 5, around 50 ppm, sample 4, around 80 ppm, sample 3, about 300 ppm, and sample 2, about 800 ppm.

Generally with exemplary sensing elements of this type comprising a total thickness (of optically responsive layer 230) of from about 400 nm to about 800 nm, the inventors have found a wavelength shift of around 80 nm to be associated with wraparound (e.g., the sensing element changing from a red color back to a green color similar to that exhibited initially by the sample in the absence of the analyte). Thus, sample 1 (in which the optically responsive layer was comprised only of a highly analyte-responsive (PIM) layer of approximately 600 nm thickness, with no minimally analyte-responsive layer being present) might be expected to exhibit wraparound upon exposure to an atmosphere containing around 100 ppm styrene. Notably, none of samples 2-7, which all contained a PIMS layer of no more than about 300 nm in thickness, and each of which contained a minimally analyte-responsive layer of such thickness as to make the total thickness of the optically responsive layer approximately 600 nm, exhibited a wavelength shift of 80 nm (which might be expected to result in wraparound), even upon exposure to relatively high levels of styrene. For instance, even sample 4, which was exposed to 1300 ppm of styrene, did not reach the 80 nm threshold.

Response of Samples 8-9 to a Test Analyte

Samples 8 and 9 were adhered using 3M 8172 (clear) optical adhesive to the inner side wall of a filtration cartridge that was of the general type shown in FIG. 6, and that was made of clear plastic. The (analyte-permeable) silver nanoparticle layer faced toward the interior of the cartridge. The cartridge was then filled with 45.8 g of activated carbon (available from Kuraray under the trade designation GG 12X20) sorbent. The samples were oriented with their length parallel to the direction of air flow through the sorbent material, at an edge of the bed of sorbent material. The cartridge was then sealed and was challenged with 1000 PPM styrene (which is fifty times the Threshold Limit Value (TLV) of styrene (20 PPM) as established by American Conference of Governmental Industrial Hygienists) in dry house air (relative humidity less than about 5%) at a flowrate of 32 liters per minute. Under ambient lighting, a Zarbeco camera (MiScope-MP) was used to monitor the sensing elements through the clear plastic side wall of the cartridge and through the clear adhesive. Prior to flow of the vapor-laden air, both sensing elements had a green appearance. After 153 minutes of exposure, sample 8 exhibited a mixture of red and green (with green predominating in the upstream (with respect to the airflow) portion of the sample), while the upstream portion of sample 9 was predominately red and the downstream portion of sample 9 was predominately green. It thus appeared that sample 9 was exhibiting a response to the analyte "front" making its way through the cartridge (upon the progressive saturation of the sorbent material by analyte), while sample 8 may have been experiencing at least some (i.e., localized) wraparound. After 228 minutes of exposure, sample 8 had returned to a uniformly green appearance (i.e., having experienced complete wraparound) while sample 9 now exhibited a uniformly red appearance (i.e., had not experienced wraparound).

The tests and test results described above are intended solely to be illustrative, rather than predictive, and variations in the testing procedure can be expected to yield different results. All quantitative values in the Examples section are understood to be approximate in view of the commonly known tolerances involved in the procedures used. The foregoing detailed description and examples have been given for clarity of understanding only. No unnecessary limitations are to be understood therefrom.

It will be apparent to those skilled in the art that the specific exemplary structures, features, details, configurations, etc., that are disclosed herein can be modified and/or combined in numerous embodiments. All such variations and combinations are contemplated by the inventor as being within the bounds of the conceived invention. Thus, the scope of the present invention should not be limited to the specific illustrative structures described herein, but rather by the structures described by the language of the claims, and the equivalents of those structures. To the extent that there is a conflict or discrepancy between this specification and the disclosure in any document incorporated by reference herein, this specification will control.

What is claimed is:

1. An array for optically detecting an analyte, the array comprising at least two individually optically interrogatable sensing elements,
    wherein each sensing element comprises an optically responsive layer between two reflective layers,
    wherein the optically responsive layer of each sensing element comprises at least a highly analyte-responsive first sublayer, and wherein the optically responsive layer of at least one of the sensing elements further comprises a minimally analyte-responsive second sublayer,
        wherein the first sublayer and the second sublayer of each sensing element each comprise a thickness, and wherein the thickness of the first sublayer and of the second sublayer of one sensing element are significantly different from the thickness of the first sublayer and of the second sublayer, respectively, of another sensing element.

2. The array of claim 1 wherein the thickness of the optically responsive layer of at least one sensing element is similar to the thickness of the optically responsive layer of at least one other sensing element.

3. The array of claim 1 wherein at least one of the sensing elements does not contain a minimally analyte-responsive second sublayer.

4. The array of claim 1 wherein at least one of the sensing elements comprises an optically responsive layer wherein the ratio of the thickness of the first, highly analyte-responsive sublayer to that of the second, minimally analyte-responsive sublayer is from about 1:8 to about 8:1.

5. The array of claim 1 wherein at least one of the sensing elements comprises an optically responsive layer wherein the ratio of the thickness of the first, highly analyte-responsive sublayer to that of the second, minimally analyte-responsive sublayer is from about 1:4 to about 4:1.

6. The array of claim 1 wherein the array comprises at least three individually optically interrogatable sensing elements, and wherein the thickness of the first sublayer and of the second sublayer of each sensing element are significantly different from the thickness of the first sublayer and of the second sublayer, respectively, of each of the other sensing elements.

7. The array of claim 1 wherein the optical response of each of the sensing elements comprises a change from a first appearance in the absence of sufficient analyte to cause the optical response, to a second appearance in the presence of a concentration of analyte in a monitored atmosphere sufficient to cause the optical response.

8. The array of claim 7 wherein the concentration of analyte sufficient to cause an optical response of at least one sensing element of the array is at least twice the concentration of analyte sufficient to cause an optical response of at least one other sensing element of the array.

9. The array of claim 7 wherein at least one sensing element of the array does not display an optical response in the presence of an analyte concentration that is at least five times the concentration of analyte sufficient to cause an optical response of at least one other sensing element of the array.

10. The array of claim 7 wherein a concentration of analyte sufficient to cause at least one sensing element of the array to change back from the second appearance to the first appearance is greater than the concentration of analyte sufficient to cause at least one other sensing element of the array to change from the first appearance to the second appearance.

11. The array of claim 7 wherein the first appearance and second appearance of each sensing element of the array is similar to the first appearance and second appearance, respectively, of each of the other sensing elements of the array.

12. The array of claim 1 wherein the analyte comprises an organic analyte.

13. The array of claim 1 wherein the highly analyte-responsive sublayer of at least one of the sensing elements comprises a material comprising a polymer of intrinsic microporosity.

14. The array of claim 1 wherein the array is used in combination with a personal respiratory protection device.

15. The array of claim 14 wherein the sensing elements of the array are positioned within an enclosure that comprises a sorbent material that can absorb the analyte.

16. The array of claim 15 wherein the sensing elements of the array are positioned within an air purifying cartridge of a personal respiratory protection device.

17. The array of claim 16 wherein the sensing elements of the array are positioned adjacent a transparent viewing port of the air purifying cartridge so as to be optically interrogatable from the exterior of the cartridge.

18. An optical method of detecting an analyte in a monitored atmosphere, comprising:
    providing an array comprising:
        at least a first sensing element that changes from a first appearance to a second appearance in the presence of a first, lower concentration of analyte in the monitored atmosphere and that changes from the second appearance back to the first appearance in the presence of a second, higher concentration of analyte; and,
        at least a second sensing element that does not change from a first appearance to a second appearance in the presence of the first, lower concentration of analyte; that in the presence of a third, intermediate concentration of analyte that is between the lower and higher concentrations, changes from a first appearance to a second appearance; and that in the presence of the second, higher concentration of analyte does not change from the second appearance back to the first appearance; and,
    exposing the array of sensing elements to an atmosphere potentially containing the analyte.

19. The method of claim 18 wherein the array comprises at least one sensing element that changes from a first appearance to a second appearance in the presence of a concentration of analyte but that does not change from the second appearance back to the first appearance in the presence of any concentration of analyte.

20. The method of claim 18 wherein the first appearances of all the sensing elements are similar to each other, and wherein the second appearances of all the sensing elements are similar to each other.

21. The method of claim 18 wherein the array of sensing elements is configured to cover a continuous concentration range of analyte without gaps, such that at any detectable concentration of analyte in the monitored atmosphere, at least one sensing element of the array displays the second appearance.

22. The method of claim 18 wherein each sensing element comprises an optically responsive layer between two reflective layers,
    wherein the optically responsive layer of each sensing element comprises at least a highly analyte-responsive first sublayer, and wherein the optically responsive layer of at least the second sensing element further comprises a minimally analyte-responsive second sublayer, wherein the first sublayer and the second sublayer of each sensing element each comprise a thickness, and wherein the thickness of the first sublayer and of the second sublayer of one sensing element are significantly different from the thickness of the first sublayer and of the second sublayer, respectively, of another sensing element.

23. The method of claim 22 wherein the highly analyte-responsive sublayer of at least one of the sensing elements comprises a material comprising a polymer of intrinsic microporosity.

24. The method of claim 18 wherein the array is used in combination with a personal respiratory protection device.

25. The method of claim 24 wherein the sensing elements of the array are positioned within an enclosure that comprises a sorbent material that can absorb the analyte.

26. The method of claim 25 wherein the sensing elements of the array are positioned within an air purifying cartridge of a personal respiratory protection device.

27. The method of claim 26 wherein the sensing elements of the array are positioned adjacent a transparent viewing port of the air purifying cartridge so as to be optically interrogatable from the exterior of the cartridge.

* * * * *

UNITED STATES PATENT AND TRADEMARK OFFICE
CERTIFICATE OF CORRECTION

Page 1 of 1

PATENT NO.        : 8,537,358 B2
APPLICATION NO.   : 13/320948
DATED             : September 17, 2013
INVENTOR(S)       : Neal A Rakow It is certified that error appears in the above-identified patent and that said Letters Patent is hereby corrected as shown below:

In the Specification

Column 14
Line 21, After "SENSORS," insert -- Docket No. 65358US002, --.

Column 19
Line 13, After "12/470,865," insert -- Docket No. 65372US002 --.

Column 19
Line 16, After "12/470,890," insert -- Docket No. 65373US002 --.

Column 19
Line 19, After "12/470,920," insert -- Docket No. 65374US002 --.

Column 19
Line 36, After "also" insert -- be --.

Signed and Sealed this
First Day of April, 2014

Michelle K. Lee
*Deputy Director of the United States Patent and Trademark Office*